United States Patent
Chang et al.

(12)

(10) Patent No.: US 7,601,520 B2
(45) Date of Patent: Oct. 13, 2009

(54) METHOD FOR RAPID IDENTIFICATION OF PORCINE INSULIN-LIKE GROWTH FACTOR 2 INTRON 7 POINT MUTATION

(76) Inventors: Hsiu-Luan Chang, No. 20, Lane 385, Nanning Rd., Neipu Township, Pingtung County (TW); Ming-Che Wu, No. 20, Lane 385, Nanning Rd., Neipu Township, Pingtung County (TW); Chia Te Chu, No. 20, Lane 385, Nanning Rd., Neipu Township, Pingtung County (TW)

( * ) Notice: Subject to any disclaimer, the term of this patent is extended or adjusted under 35 U.S.C. 154(b) by 163 days.

(21) Appl. No.: 11/598,659

(22) Filed: Nov. 14, 2006

(65) Prior Publication Data

US 2008/0124715 A1     May 29, 2008

(51) Int. Cl.
   *C12Q 1/68*      (2006.01)
   *C12P 19/34*    (2006.01)
   *C07H 21/04*    (2006.01)

(52) U.S. Cl. .......................... 435/91.2; 435/6; 536/22.1; 536/24.31

(58) Field of Classification Search .................... 435/6, 435/91.2; 536/22.1, 24.31
See application file for complete search history.

(56) References Cited

U.S. PATENT DOCUMENTS 6,846,632 B2    1/2005  Chang et al.

OTHER PUBLICATIONS

Van Laere et al., Nature, 2003, vol. 425, p. 832-836.*
Rust et al. Nucleic acid research, 1993, vol. 21(16), p. 3623-3629.*
Buck et al. BioTechniques, 1999, vol. 27(3).*
The search report for SEQ ID No. s 4-5.*

* cited by examiner

*Primary Examiner*—Kenneth R. Horlick
*Assistant Examiner*—Joyce Tung
(74) *Attorney, Agent, or Firm*—Rosenberg, Klein & Lee

(57) ABSTRACT

A method for rapidly identifying a point mutation in porcine insulin-like-growth factor 2 intron 7 uses published primers to amplify the target DNA fragments by polymerase chain reaction. The DNA fragments are cloned and sequenced for confirmation and method validation. The key positions of the sequence are modified to generate three primers for amplifying different DNA fragments with different genotypes by PCR to avoid additional restriction enzyme digestion. A long primer is used to specifically amplify the lean muscle mass-enhancing allele, a short primer is used to specifically amplify the lean muscle mass-suppressing allele, and the third primer is shared and anneals to the complementary strand. After PCR and electrophoresis, samples with only the 92 bp band are identified as the CC genotype, samples with only the 72 bp band are identified as the GG genotype, and samples with both 92 bp and 72 bp bands are identified as heterozygotes.

5 Claims, 3 Drawing Sheets extracting DNA polymerase chain reaction electrophoresis identification

SEQUENCE LISTING

<160> NUMBER OF SEQ ID NOS: 5

<210> SEQ ID NO 1
<211> LENGTH: 72
<212> TYPE: DNA
<213> ORGANISM: Sus
<220> FEATURE:
<223> OTHER INFORMATION: C Allele Of Pig, Species Could Not Be
      Determined

<400> SEQUENCE: 1
ctccgagggt ctgagacttc agaccggggg cgccctggcc gtgcgcattg attggcacct    60
gccatgtgcc tg                                                       72

<210> SEQ ID NO 2
<211> LENGTH: 72
<212> TYPE: DNA
<213> ORGANISM: Sus
<220> FEATURE:
<223> OTHER INFORMATION: G Allele Of Pig, Species Could Not Be
      Determined

<400> SEQUENCE: 2
ctccgagggt ctgagacttc agagcggggg cgccctggcc gtgcgcattg attggcacct    60
gccatgtgcc tg                                                       72

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
tctctgtctc tctgtttctc tcccgagggt ctgagacttc atac                    44

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
ctccgagggt ctgagacttc agag                                          24

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
caggcacatg gcaggtgcca atcaatg                                       27

METHOD FOR RAPID IDENTIFICATION OF PORCINE INSULIN-LIKE GROWTH FACTOR 2 INTRON 7 POINT MUTATION

BACKGROUND OF THE INVENTION

1. Field of the Invention

The present invention relates to a method for rapidly identifying porcine insulin-like-growth factor 2 intron 7 point mutation (IGF2-in7-C162G) and, more particularly, to use a method for sorting stud pigs by IGF2-in7-C162G genotypes.

2. Description of the Related Art

Pigs are valuable livestock and improvement in the stud pigs for enhancing productivity is important to those who breed pigs at high costs. Conventional ways of sorting stud pigs by shapes have reached a bottleneck. On the other hand, rapid development in molecular biological techniques focusing on sorting of genes controlling growth characteristics has allowed putting various genes advantageous to productivity in a single animal, thereby enhancing the efficiency and accuracy in stud pig selection. A method named "Auxiliary Sorting of Inheritance Marker", which combines molecular biological techniques and quantity inheritance assessing theory for strategic gene sorting, is particularly useful in sorting out propagating characteristics with low inheritance variation and carcass characteristics requiring high assessing costs. An example for identifying stud pigs with high reproductive potential is disclosed in U.S. Pat. No. 6,846,632, which teaches a method for rapidly identifying porcine estrogen receptor marker by mutagenically separated polymerase chain reaction (MS-PCR).

Besides productivity, another value index for pigs is the quality of meat production, which is the primary index for the production effect of livestock. Selection of male stud pigs aiming to increase the muscle mass of domestic pigs and to improve the lean meat percentage of carcass is the common goal to the pig breeding industry and the carcass processing industry. Meat quality and meat quantity are controlled by multiple genes. However, literatures on the genes and the interaction among various genes are scarce.

Only few references discussed genes regarding carcass characteristics of meat production quantity and quality of pigs; these genes include stress gene (Fujii et al., 1991), acid meat gene (R N, Ciobanu et al., 2001; Milan et al., 2000), MC4R gene (Kim et al., 2000), and insulin-like-growth factor 2 (IGF2) gene (van Laere et al., 2003).

The protein of IGF2 affects growth of cells. The porcine IGF2 gene is located on 2pl.7 of the second chromosome. The gene is 23,821 base pairs in length and is composed of four promoters, ten exons, and nine introns.

According to research results, the single nucleotide polymorphism (SNP) in IGF2-in3-G3072A of pigs is a quantitative trait nucleotide (QTN) that mainly affects quantitative trait of muscle quantity and fat accumulation of pigs. Thus, A allele in the IGF2-in3-3072 position is accompanied by the characteristics of high muscle quantity and low fat accumulation (Jeon et al., 1999; Nezer et al., 1999; van Laere et al., 2003; Jungerius et al., 2004). However, Detection of the polymorphism utilizes real-time polymerase chain reaction (Carrodeguas et al., 2005) or minisequencing (SnaPshot, Vykoukalova et al., 2006). The procedures are complicated and inefficient; therefore, improvement is required.

SUMMARY OF THE INVENTION

The primary objective of the present invention is to provide a method for rapidly identifying porcine insulin-like-growth factor 2 intron 7 point mutation and use the point mutation as a marker for stud pig selection.

In accordance with the method of the present invention, the DNA fragment is cloned and sequenced. The key positions of the sequence are modified to generate three primers which are used to amplify DNA fragments representing different genotypes to avoid the need for subsequent restriction enzyme digestion. The long primer is to specifically amplify the C allele which enhances lean muscle mass production; the short primer is to specifically amplify the G allele which suppresses lean muscle mass production; the third primer is shared by both alleles and anneals to the complementary strand. After PCR and electrophoresis, samples with only the 92 bp band are identified as having the CC allele (muscular phenotype), samples with only the 72 bp band are identified as having the GG allele (non-muscular phenotype), and samples with both 92 and 72 bp bands are identified as heterozygous.

Genotype analysis on Landrace, Yorkshire, and Duroc pigs in Central Inspection Station of Taiwan found the presence of the porcine insulin like growth factor 2 intron 7 point mutation (IGF2 in7 C162G).

Further comparison in stud pig performance showed that the CC genotype in the three types of pigs mentioned above have the highest possibility of earning the highest inspection indices of champion pigs at various inspections. On the other hand, the stud pigs of GG genotype have higher average fat thickness in the back, which is indicative of low possibility of lean meat. Furthermore, the qualifying rate of stud pigs with a CC genotype is far better than that of stud pigs with a GG genotype, which means CC genotype is of advantageous.

Other objectives, advantages, and features of the invention will become more apparent from the following detailed description when taken in conjunction with the accompanying drawings.

DETAILED DESCRIPTION OF THE PREFERRED EMBODIMENT

The present invention provides a method for rapidly identifying porcine insulin-like-growth factor 2 intron 7 (IGF2-in7-C162G) point mutation by mutagenically separated polymerase chain reaction (MS-PCR). Three primers are designed for detecting the normal and the mutant allele (generally point mutation). The long primer C (the C primer) is used to specifically amplify the allele that enhances lean muscle mass production; the short primer G (the G primer) is used to specifically amplify the allele that suppresses lean muscle mass production; the R primer is shared by both alleles for the PCR amplification. Extracted DNA sample and the three primers as well as other compounds are placed in a test tube and placed in a temperature circulator for carrying out polymerase chain reaction (PCR). The genotype of the sample can be identified by agarose gel electrophoresis of the PCR products. As a result, samples showing only the 92 bp fragment have the CC genotype and samples with only the 72 bp fragment have the GG genotype. Samples with both the 92 and the 72 bp fragments are heterozygous with the GC genotype.

Figure 1:
FIG. 1 is a flowchart showing the method for rapidly identifying porcine insulin-like-growth factor 2 intron 7 point mutation in accordance with the present invention.
Figure 1:
Figure 1:

As illustrated in FIG. 1, the first step of the method in accordance with the present invention is DNA extraction from the samples. DNA can be extracted from blood, internal organs, muscular tissues, or semen. Of more importance, the DNA sample contains the sequence for insulin-like-growth factor 2 intron 7. The double-stranded DNA is heated at high temperature and separated into single-stranded DNA that acts as a template for PCR.

The reactive substance for PCR includes 80-100 ng of the single-stranded DNA sample and a solution consists of 0.8 mM deoxy-nucleotide-triphosphates (dNTP, at 0.2 mM of each dATP, dCTP, dGTP, and dTTP), 0.4-0.6 μM (preferably 0.5 μM) C primer, 0.8-1.2 μM (preferably 1.0 μM) G primer, 0.8-1.2 μM (preferably, 1.0 μM) R primer, 2 mM $MgCl_2$, 1×PCR buffer (75 mM Tris-HCl, pH 9.0, 2 mM $MgCl_2$, 20 mM $(NH_4)_2SO_4$, and 50 mM KCl), 0.1 mM cresol red (in 20% sucrose solution), and 1 unit of Taq DNA polymerase. The total volume of the PCR reaction is 10 μl.

The primer sequences are as follows:

```
The C primer:
5'-TCTCTGTCTCTCTGTTTCTCTCCCGAGGGTCTGAGACTTCATAC-3'

The G primer:
5'-CTCCGAGGGTCTGAGACTTCAGAG-3'.

The R primer:
5'-CAGGCACATGGCAGGTGCCAATCAATG-3'.
```

The primers are capable of locating the target sequences in the template.

In the first cycle of the mutagenically separated polymerase chain reaction (MS-PCR), the temperature and time are set as follows: 95±1° C., 110-150 seconds. In the next 25 cycles, the temperature and time are set as follows: 95° C., 20 seconds; 57° C., 10 seconds; 72° C., 20 seconds. The variation for the time is ±5%, and the variation for the temperature is ±1° C. At the end, the reaction is held for 2 minutes (or 110-150 seconds) at 72±1° C.

The PCR products are then separated by agarose gel electrophoresis. Samples with only the 92 bp band are identified as having the CC genotype, sample with only the 72 bp band are identified as having the GG genotype, and samples with both 92 and 72 bp bands are identified as heterozygotes.

Thus, the genotype of the pig can be identified by the size of the PCR product in one simple reaction.

The primer design in MS-PCR produces different size PCR fragments for different genotypes, thereby, eliminating the need for restriction enzyme digestion.

Figure 2:
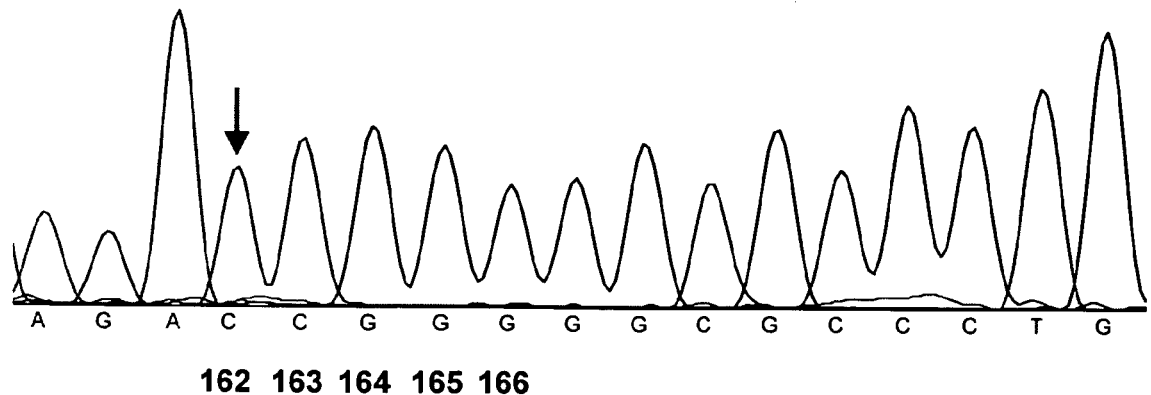
FIG. 2 is a diagram showing the DNA sequence encompassing the C allele in IGF2-in7-162.
Figure 3:
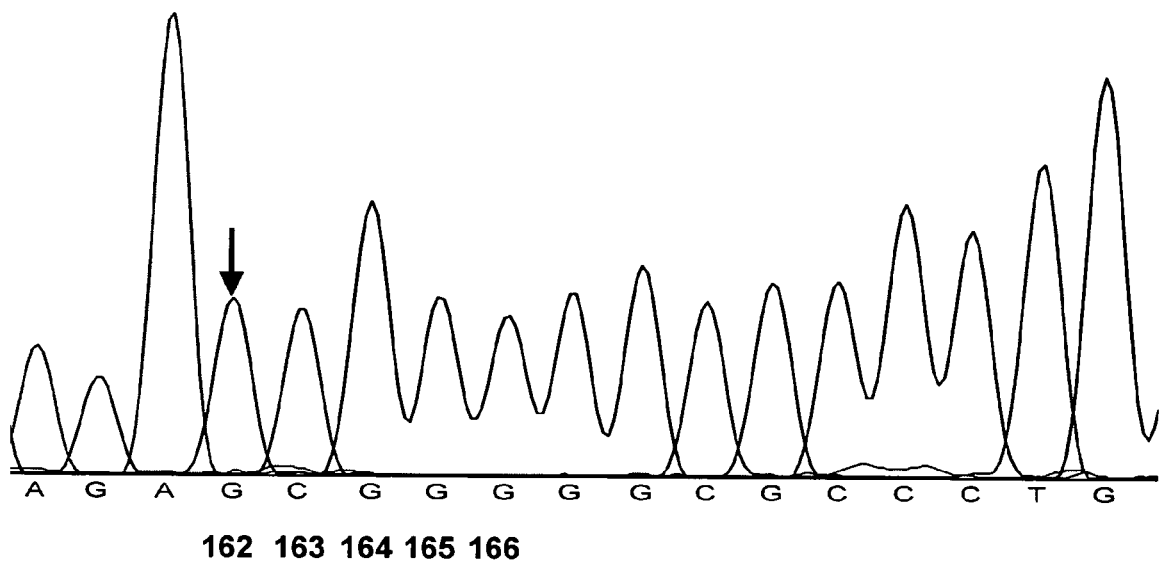
FIG. 3 is a diagram showing the DNA sequence encompassing the G allele in IGF2-in7-162.

In FIG. 2, the partial sequence of a DNA fragment containing the lean muscle mass-enhancing SNP is shown. The DNA sequence from nt 162-166 of IGF2 intron 7 is CCGGG, which can be cut by the restriction enzyme NciI. In FIG. 3, the partial sequence of a DNA fragment containing the lean muscle mass-suppressing SNP is shown. The DNA sequence from nt 162-166 of IGF2 intron 7 is GCGGG, which cannot be cut by the restriction enzyme NciI.

To identify the SNP genotype illustrated in FIGS. 2 and 3, PCR-RFLP (polymerase chain reaction-restriction fragment length polymorphism) and MS-PCR (mutagenically separated PCR) can be used. In PCR-RFLP (FIG. 4), a specific DNA fragment (885 bp fragment) containing the SNP is amplified by PCR, and the presence or absence of the restriction site (NciI) is then analyzed by restriction enzyme digestion. The C allele makes the PCR fragment susceptible to NciI digestion and generates a smaller DNA fragment (785 bp) after NciI digestion; the presence of G allele makes the PCR fragment resistant to NciI digestion and retain the 885 bp fragment after the digestion. The analysis thus generates various lengths of restriction DNA fragments (RFLP) according to the SNP genotype. PCR-RFLP is a rapid method, suitable for the identification of parental lineage in samples and for the analysis of gene variations in clinical medicine.

MS-PCR on the other hand, includes the design of three primers in association with the DNA sequence and the SNP positions (generally for point mutation). Components for PCR reaction are prepared and placed in a specific tube, which is then placed in a temperature circulator for subsequent PCR reactions. The genotype can be identified by the presence of different sizes of PCR fragments (FIG. 5) after electrophoresis.

Figure 4:
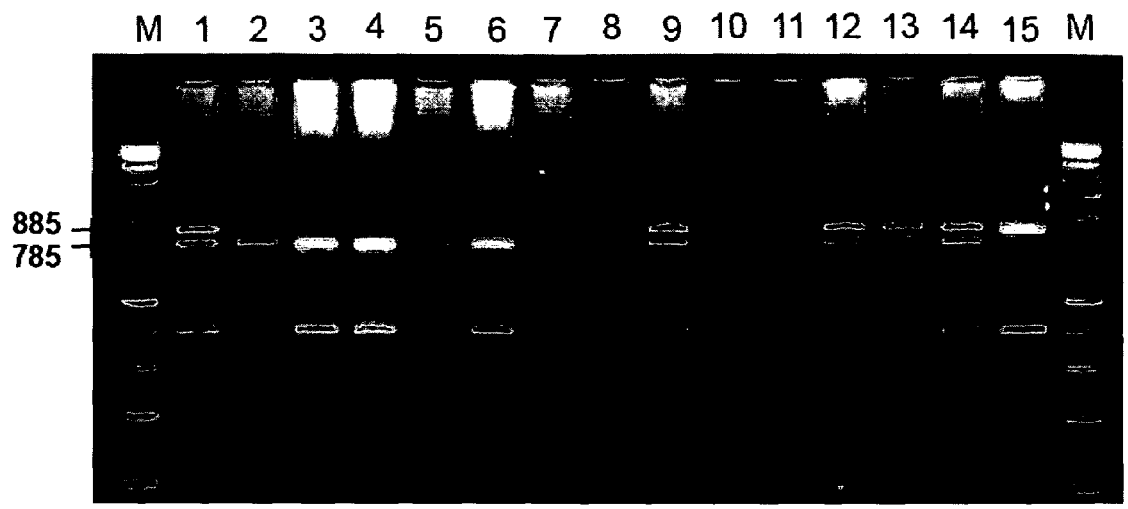
FIG. 4 is a picture showing the IGF2-in7-162 genotype results using PCR-RFLP.
Figure 5:
FIG. 5 is a picture showing the IGF2-in7-162 genotype results using MS-PCR.

FIGS. 4 and 5 show the results of the SNP analysis in the IGF2 intron 7 nt 162 using PCR-RFLP and MS-PCR, respectively. M indicates molecular weight standards and numbers 1-15 indicate different DNA samples. Samples in lanes 1, 5, 8, 9, and 11-14 are heterozygous (CG), samples in lanes 2-4, 6, 7, and 10 are homozygous CC, and samples in lane 15 is homozygous GG.

As shown in Table 1, the cost and time for genotyping is saved by ⅓ and ½, respectively, when MS-PCR is used. Hence, the method using MS-PCR in accordance with the present invention saves time and cost while allowing pig breeder to use this method for mass identification of stud pigs.

TABLE 1

Time for operation and cost for material per sample between PCR-FRLP and MS-PCR

|  | PCR-PFLP | | MS-PCR | |
| --- | --- | --- | --- | --- |
|  | Time (Min) | Cost ($NT) | Time (Min) | Cost ($NT) |
| DNA extraction | 6 | 20 | 6 | 20 |
| PCR | 8 | 15 | 4 | 15 |
| Restriction enzyme digestion | 12 | 50 | 0 | 0 |
| Electrophoresis and identification | 4 | 10 | 4 | 30 |
| Total | 30 | 95 | 14 | 65 |

Although the invention has been explained in relation to its preferred embodiment, it is to be understood that many other possible modifications and variations can be made without departing from the scope of the invention as hereinafter claimed.

What is claimed is:

1. A method for rapidly identifying a point mutation in porcine insulin-like-growth factor 2 intron 7 by a mutagenically separated polymerase chain reaction, the method comprising the steps of:
   (a) extracting a DNA sample from a pig to be identified, the DNA sample including insulin-like-growth factor 2 intron 7;
   (b) proceeding with a polymerase chain reaction by combining the DNA sample with a solution comprising:
   a first primer (C primer), wherein said C primer is the DNA sequence:
   5'TGTCTGTCTCTCTGTTTCTCTC-CCGAGGGTCTGAGACTTCATAC-3' (SEQ ID NO: 3),
   a second primer (G primer), wherein said G primer is the DNA sequence:
   5'-CTCCGAGGGTCTGAGACTTCAGAG-3' (SEQ ID NO: 4),
   a third primer (K primer), wherein said R primer is the DNA sequence:
   5'-CAGGCACATGGCAGGTGCCAATCAATG-3' (SEQ ID NO: 5), and
   a reaction mixture required for polymerase chain reaction, the first primer amplifying a lean muscle mass-enhancing allele, the second primer amplifying a lean muscle mass-suppressing allele, and the third primer being the third primer is shared by the first primer and the second primer in the PCR reactions; and
   (c) electrophoresizing a product resulting from step (b) to thereby identify the DNA sample by a band of the DNA sample, in which the DNA sample is identified as muscular genotype when having 92 bp band, the sample is identified as non-muscular genotype when having 72 bp band, and the sample is identified as hetero-genotype when having both 92 bp and 72 bp bands.

2. The method as claimed in claim 1 wherein the DNA sample is of 80-100 ng, and wherein the solution includes 0.8 mM deoxy-nucleotide-triphosphates (dNTP), 0.4-0.6 µM C primer, 0.8-1.2 µM G prima, 0.8-1.2 µM K primer, a reaction mixture containing magnesium ion, 1×PCR buffer (75 mM Tris-HCl, pH 9.0, 2 mM $MgCl_2$, 20 mM $(NH_4)_2SO_4$, and 50 mM KCl of 50 mM), 0.1 mM cresol red (in 20% sucrose), and one unit of Taq DNA polymerase.

3. The method as claimed in claim 1, wherein, in a first cycle of the mutagenically separated polymerase chain reaction, the temperature and time are set as follows: 95±1° C., 110-150 seconds, wherein the temperature and time in next 25 cycles are set as follows: 95° C., 20 seconds; 57° C., 10 seconds; 72° C., 20 seconds, the variation for the time is ±5%, and the variation for the temperature is ±1° C., and wherein a final reaction is held for 110-150 seconds at 72±1° C.

4. The method as claimed in claim 1 wherein the magnesium ion has a concentration of 2.0 mM and is from magnesium chloride.

5. The method as claimed in claim 2 wherein the C primer has a concentration of 0.50 µM, the C primer has a concentration of 1.0 µM, and the R primer has a concentration of 1.0 µM.

* * * * *